(12) United States Patent
Chen

(10) Patent No.: US 9,199,909 B2
(45) Date of Patent: *Dec. 1, 2015

(54) HYDROCONVERSION OF RENEWABLE FEEDSTOCKS

(75) Inventor: Cong-Yan Chen, Kensington, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 880 days.

This patent is subject to a terminal disclaimer.

(21) Appl. No.: 13/315,729

(22) Filed: Dec. 9, 2011

(65) Prior Publication Data

US 2013/0150636 A1    Jun. 13, 2013

(51) Int. Cl.
| | |
|---|---|
| *C07C 1/00* | (2006.01) |
| *C07C 67/00* | (2006.01) |
| *C10G 3/00* | (2006.01) |
| *C07C 29/17* | (2006.01) |
| *C07C 27/04* | (2006.01) |

(52) U.S. Cl.
CPC ............ *C07C 67/00* (2013.01); *C07C 27/04* (2013.01); *C07C 29/177* (2013.01); *C10G 3/46* (2013.01); *C10G 3/50* (2013.01); *C10G 2300/1014* (2013.01)

(58) Field of Classification Search
CPC ............ C10G 3/42; C10G 3/46; C10G 11/02; C10G 45/60; C10G 45/36; C10G 2300/1011; C10G 2300/1055; C10G 2300/1088; C10G 2300/70; Y02E 50/14
USPC .................................. 585/240, 242; 44/605
See application file for complete search history.

(56) References Cited

U.S. PATENT DOCUMENTS

| | | | | |
|---|---|---|---|---|
| 4,992,605 | A * | 2/1991 | Craig et al. ................... | 585/240 |
| 5,366,658 | A | 11/1994 | Hoppe et al. | |
| 6,162,350 | A * | 12/2000 | Soled et al. ................... | 208/113 |
| 7,544,850 | B2 | 6/2009 | Goze | |
| 7,667,059 | B2 | 2/2010 | Sakamoto et al. | |
| 7,888,542 | B2 | 2/2011 | Koivusalmi | |
| 8,097,740 | B2 | 1/2012 | Miller | |
| 8,324,438 | B2 | 12/2012 | Brandvold | |
| 8,704,007 | B2 * | 4/2014 | Chen et al. ................... | 568/864 |
| 8,809,610 | B2 * | 8/2014 | Van Beijnum et al. ....... | 585/733 |
| 8,816,143 | B2 * | 8/2014 | Miller ........................... | 585/240 |
| 2006/0207166 | A1 | 9/2006 | Herskowitz et al. | |
| 2007/0161832 | A1 | 7/2007 | Myllyoja et al. | |
| 2009/0166256 | A1 | 7/2009 | Lewis | |
| 2009/0255171 | A1 | 10/2009 | Dumesic | |
| 2010/0076236 | A1 * | 3/2010 | Van Heuzen et al. ......... | 585/313 |
| 2010/0263263 | A1 | 10/2010 | O'Rear | |
| 2011/0015459 | A1 | 1/2011 | Aalto et al. | |
| 2011/0047862 | A1 | 3/2011 | Mayeur | |
| 2011/0155636 | A1 | 6/2011 | Hanks | |
| 2012/0000824 | A1 | 1/2012 | Dougherty | |
| 2012/0016167 | A1 | 1/2012 | Hanks | |
| 2012/0053099 | A1 | 3/2012 | Zhou | |
| 2012/0216450 | A1 | 8/2012 | Dupassieux | |
| 2012/0283151 | A1 | 11/2012 | Espagne | |

FOREIGN PATENT DOCUMENTS

WO    WO 2009/156452    * 12/2009

OTHER PUBLICATIONS

D. Kubicka and L. Kaluza "Deoxygenation of vegetable oils over sulfided Ni, Mo and NiMo catalysts" Appl. Catal. A 372, 199-208 (2010).
PCT/US2012/068621, Written Opinion and Search Report, mail date Mar. 29, 2013, 12 pages.
Chen, Cong-Yan, *Hydroconversion of Renewable Feedstocks*, U.S. Appl. No. 13/315,650, filed Dec. 9, 2011.
Chen, Cong-Yan, *Hydroconversion of Renewable Feedstocks*, U.S. Appl. No. 13/315,611, filed Dec. 9, 2011.
Chen, Cong-Yan, *Hydroconversion of Renewable Feedstocks*, U.S. Appl. No. 13/315,683, filed Dec. 9, 2011.
Chen, Cong-Yan, *Hydroconversion of Renewable Feedstocks*, U.S. Appl. No. 13/315,575, filed Dec. 9, 2011.
Chen, Cong-Yan, *Hydroconversion of Renewable Feedstocks*, U.S. Appl. No. 13/315,774, filed Dec. 9, 2011.
Chen, Cong-Yan, *Hydroconversion of Renewable Feedstocks*, U.S. Appl. No. 13/708,811, filed Dec. 7, 2012.

* cited by examiner

*Primary Examiner* — Nina Bhat
(74) *Attorney, Agent, or Firm* — Melissa M. Hayworth; Terrence M. Flaherty

(57) ABSTRACT

A hydrocarbon conversion process comprises contacting a renewable feedstock under hydroprocessing conditions with supported catalyst comprising at least one metal selected from the group consisting of Group VIII metals, Group VIB metals to form oleochemicals such as fatty alcohols, esters, and normal paraffins. Advantageously, the reaction conditions can be selected to directly convert the renewable feedstock to the desired product(s).

15 Claims, No Drawings

HYDROCONVERSION OF RENEWABLE FEEDSTOCKS

TECHNICAL FIELD

The application relates generally to a process for converting renewable feedstocks to oleochemicals such as fatty alcohols, esters, and normal paraffins by contacting the feedstock with a supported metal catalyst under hydroprocessing conditions.

BACKGROUND

Fossil fuels are a finite, non-renewable resource formed from decayed plants and animals that have been converted to crude oil, coal, natural gas, or heavy oils by exposure to heat and pressure in the earth's crust over hundreds of millions of years. However, as the world's petroleum resources are depleting coupled with its ever-increasing prices, many industries worldwide have been looking into renewable/sustainable raw materials to replace petroleum-based materials in their manufacturing processes.

Industrial oleochemicals are useful in the production of surfactants, lubricants, fuels, plastics, and the like. Oleochemicals include, but are not limited to, fatty alcohols, esters and paraffins. Providing efficient processes for directly converting renewable materials into such products would be highly desirable.

SUMMARY

In one aspect, there is provided a hydrocarbon conversion process comprising contacting a renewable feedstock, under hydroprocessing conditions, with a supported catalyst comprising at least one metal selected from the group consisting of Group VIII metals, Group VIB metals to form an effluent and recovering a fatty alcohol fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

In another aspect, there is provided a hydrocarbon conversion process comprising contacting a renewable feedstock, under hydroprocessing conditions, with a supported catalyst comprising at least one metal selected from the group consisting of Group VIII metals, Group VIB metals to form an effluent and recovering an aliphatic monoester fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

In yet another aspect, there is provided hydrocarbon conversion process comprising contacting a renewable feedstock, under hydroprocessing conditions, with a supported catalyst comprising at least one metal selected from the group consisting of Group VIII metals, Group VIB metals to form an effluent and recovering a hydrocarbon fraction comprising normal paraffins from the effluent, wherein the hydroprocessing conditions include a temperature of from 491° F. to 662° F. (255° C. to 350° C.) and a total reaction pressure of from 800 to 2000 psig (5.5 to 13.8 MPa gauge).

DETAILED DESCRIPTION

The following terms will be used throughout the specification and will have the following meanings unless otherwise indicated.

The term "renewable feedstock" is meant to include feedstocks other than those obtained from crude oil.

The term "oleochemical" refers to a chemical that is biologically-derived, i.e., from a renewable resource of biological origin. Such a term is generally accepted as being exclusive of fossil fuels.

A "middle distillate" is a hydrocarbon product having a boiling range of from 250° F. to 1100° F. (121° C. to 593° C.). The term "middle distillate" includes the diesel, heating oil, jet fuel, and kerosene boiling range fractions. It may also include a portion of naphtha or light oil. A "jet fuel" is a hydrocarbon product having a boiling range in the jet fuel boiling range. The term "jet fuel boiling range" refers to hydrocarbons having a boiling range of from 280° F. to 572° F. (138° C. to 300° C.). The term "diesel fuel boiling range" refers to hydrocarbons having a boiling range of from 250° F. to 1000° F. (121° C. to 538° C.). The "boiling range" is the 10 vol. % boiling point to the final boiling point (99.5 vol. %), inclusive of the end points, as measured by ASTM D2887-08 ("Standard Test Method for Boiling Range Distribution of Petroleum Fractions by Gas Chromatography").

The term "triglyceride," refers to class of molecules having the general formula (1):

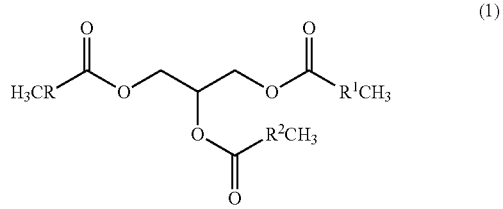

wherein R, $R^1$ and $R^2$ are independently aliphatic residues having from 6 to 22 carbon atoms (e.g., from 8 to 20 carbon atoms, or from 10 to 16 carbon atoms). The term "aliphatic" means a straight (i.e., un-branched) or branched, substituted or un-substituted hydrocarbon chain that is completely saturated or that contains one or more units of unsaturation.

The term "fatty alcohol" refers to primary aliphatic alcohols generally having from 8 to 24 carbon atoms, usually from 8 to 18 carbon atoms.

The term "aliphatic monoester" refers to compounds having the general formula (2):

wherein $R^3$ and $R^4$ are independently alkyl moieties, $R^4$ is an alkyl moiety having at least 8 carbon atoms, and the total carbon number of the aliphatic monoester is at least 14. In some embodiments, the aliphatic ester has from 16 to 40 carbon atoms (e.g., from 18 to 36, or from 20 to 34 carbon atoms). Such esters can be useful as lubricants.

The term "paraffin" refers to any saturated hydrocarbon compound, i.e., an alkane having the formula $C_nH_{(2n+2)}$ where n is a positive non-zero integer.

The term "normal paraffin" refers to a saturated straight chain hydrocarbon.

The term "isoparaffin" refers to a saturated branched chain hydrocarbon.

The term "hydroconversion" can be used interchangeably with the term "hydroprocessing" and refers to any process that is carried out in the presence of hydrogen and a catalyst. Such processes include, but are not limited to, methanation, water gas shift reactions, hydrogenation, hydrotreating, hydrodesulfurization, hydrodenitrogenation, hydrodeoxygenation, hydrodemetallation, hydrodeoxygenation, hydrodearomatization, hydroisomerization, hydrodewaxing and hydrocracking including selective hydrocracking.

The term "supported catalyst" refers a catalyst in which the active components, in this case Group VIII and Group VIB metals or compounds thereof, are deposited on a carrier or support.

When used herein, the Periodic Table of the Elements refers to the version published by the CRC Press in the *CRC Handbook of Chemistry and Physics,* 88th Edition (2007-2008). The names for families of the elements in the Periodic Table are given here in the Chemical Abstracts Service (CAS) notation.

The term "isomerizing" refers to catalytic process in which a normal paraffin is converted at least partially into an isoparaffin. Such isomerization generally proceeds by way of a catalytic route.

The term "conversion" refers to the amount of triglycerides in the feed that is converted to compounds other than triglycerides. Conversion is expressed as a weight percentage based on triglycerides in the feed. "Selectivity" is expressed as a weight percent based on converted triglycerides. It should be understood that each compound converted from triglycerides has an independent selectivity and that selectivity is independent from conversion.

Feed

The renewable feedstocks that can be used include any of those which comprise triglycerides. The feedstock generally originates from a biomass source selected from the group consisting of crops, vegetables, microalgae, animal fats, and combinations thereof. The feedstock generally comprises at least 25 wt. % triglycerides (e.g., at least 50 wt. %, 75 wt. %, 90 wt. %, or 95 wt. % triglycerides). Those of skill in the art will recognize that generally any biological source of lipids can serve as the biomass from which the feedstock can be obtained. It will be further appreciated that some such sources are more economical and more amenable to regional cultivation, and also that those sources from which food is not derived can be additionally attractive (so as not to be seen as competing with food). Exemplary feedstocks include, but are not limited to canola oil, coconut oil, palm oil, palm kernel oil, peanut oil, rapeseed oil, soybean oil, and the like.

Hydroprocessing Catalyst

Hydrotreating catalysts are suitable for hydroconversion of renewable feedstocks. Such catalysts comprise at least one metal component selected from Group VIII metals and/or at least one metal component selected from the Group VIB metals. Group VIII metals include iron (Fe), cobalt (Co) and nickel (Ni). The noble metals, especially palladium (Pd) and/or platinum (Pt), can be included in the hydrotreating catalyst. Group VIB metals include chromium (Cr), molybdenum (Mo) and tungsten (W). Group VIII metals can present in the catalyst in an amount of from 0.5 to 25 wt. % (e.g., from 2 to 20 wt. %, 3 to 10 wt. %, 5 to 10 wt. %, or 5 to 8 wt. %) and Group VIB metals can be present in the catalyst in an amount of from 0.5 to 25 wt. % (e.g., from 5 to 20 wt. %, or 10 to 15 wt. %), calculated as metal oxide(s) per 100 parts by weight of total catalyst, where the percentages by weight are based on the weight of the catalyst before sulfiding. The total weight percent of metals employed in the hydrotreating catalyst is at least 15 wt. %. The remainder of the catalyst can be composed of the support material, although optionally other components may be present (e.g., filler, cracking component, molecular sieve, or the like, or a combination thereof).

The metal components in the catalyst can be in the oxide and/or the sulfide form. If a combination of at least a Group VIII and a Group VIB metal component is present as (mixed) oxides, it can be subjected to a sulfiding treatment prior to proper use in hydroprocessing. Suitably, the catalyst usually comprises one or more components of Ni and/or Co and one or more components of Mo and/or W.

The hydrotreating catalyst can be prepared by blending, or co-mulling, active sources of the aforementioned metals with a binder. Examples of binders include silica, silicon carbide, amorphous and crystalline silica-aluminas, silica-magnesias, aluminophosphates, boria, titania, zirconia, and the like, as well as mixtures and co-gels thereof. Preferred supports include silica, alumina, alumina-silica, and the crystalline silica-aluminas, particularly those materials classified as clays or zeolitic materials. Especially preferred support materials include alumina, silica, and alumina-silica, particularly either alumina or silica. Other components, such as phosphorous, can be added as desired to tailor the catalyst particles for a desired application. The blended components can then shaped, such as by extrusion, dried and calcined at temperatures up to 1200° F. (649° C.) to produce the finished catalyst. Alternatively, other methods of preparing the amorphous catalyst include preparing oxide binder particles, such as by extrusion, drying and calcining, followed by depositing the aforementioned metals on the oxide particles, using methods such as impregnation. The catalyst, containing the aforementioned metals, can then further dried and calcined prior to use as a hydrotreating catalyst.

In some such embodiments, the active metal catalyst component is selected from the group consisting of a Ni—Mo catalyst, a Ni—W catalyst, a Ni—Mo—W catalyst, a Co—Mo catalyst, and combinations thereof. In some particular embodiments, the hydroprocessing step makes use of an alumina-supported Ni—Mo catalyst.

In some embodiments, the catalyst is characterized by an average pore size of from 1 to 10 nm (e.g., from 5 to 10 nm) and a surface area of from 20 to 400 m$^2$/g (e.g., from 100 to 300 m$^2$/g).

Hydroprocessing Conditions

The hydroprocessing conditions can be selected so that an overall conversion rate of triglycerides in the feedstock is at least 50 wt. %, (e.g., at least 60 wt. %, 70 wt. %, 80 wt. %, 90 wt. %, or 95 wt. %). Suitable hydroprocessing conditions can include a temperature of from 383° F. to 662° F. (195° C. to 350° C.), e.g., from 383° F. to 464° F. (195° C. to 240° C.), 491° F. to 662° F. (255° C. to 350° C.), or from 491° F. to 563° F. (255° C. to 295° C.); a total reaction pressure of from 500 to 2000 psig (3.4 to 13.8 MPa gauge), e.g., from 800 to 2000 psig (5.5 to 13.8 MPa gauge), or from 1600 to 2000 psig (11.0 to 13.8 MPa gauge); a liquid hourly space velocity (LHSV) of from 0.1 to 5 h$^{-1}$, e.g., from 0.5 to 2 h$^{-1}$; and a hydrogen feed rate of from 0.1 to 20 MSCF/bbl (thousand standard cubic feet per barrel), e.g., from 1 to 10 MSCF/bbl. Note that a feed rate of 10 MSCF/bbl is equivalent to 1781 L H$_2$/L feed.

The hydroprocessing process can be single-staged or multiple-staged. In one embodiment, the process utilizes a single-stage system. Catalysts prepared from the catalyst precursor can be applied in any reactor type. In one embodiment, the catalyst is applied to a fixed bed reactor.

If desired, unreacted triglycerides can be recycled to the reaction system for further processing to maximize production of the desired product(s).

Products

The effluent from the hydroprocessing zone will comprise a liquid portion and a gaseous portion. After hydroprocessing, the effluent can be passed to one or more separators/fractionators for the removal of gas phase products (e.g., CO, $CO_2$, methane and propane) and separation of one or more fully and/or partially deoxygenated product fractions (e.g., n-paraffins, fatty alcohols and/or aliphatic monoesters) from the liquid portion. Different feedstocks will result in different carbon distributions of liquid products.

In one embodiment the liquid product is a product selected from the group of a fatty alcohol, an aliphatic monoester, and normal paraffins. In another embodiment, the product is a fatty alcohol, an aliphatic monoester, or a combination thereof. The hydroprocessing conditions can be selected from any parameter that influences the subsequent level of the desired product(s) in the effluent from the reactor. In one aspect, the hydroprocessing parameter is one that obtains a yield of a product in the reactant mixture, increases the yield of a product, optimizes the selectivity of products in the reactor, or is effective for a conversion of triglycerides in the reactor. In one embodiment, the hydroprocessing parameter is selected from the group consisting of a reactor temperature, a reactor pressure and combinations thereof.

In some embodiments, the effluent comprises a fatty alcohol fraction. In some embodiments, the effluent comprises at least 20 wt. % of a fatty alcohol (e.g., at least 25 wt. %, 30 wt. %, 30 wt. %, 35 wt. %, 40 wt. %, or 45 wt. % of a fatty alcohol). In some embodiments, the effluent has a selectivity to a fatty alcohol of at least 30% (e.g., at least 35%, 40%, or 45%).

In some embodiments, the effluent comprises an aliphatic monoester fraction. In some embodiments, the effluent comprises at least 20 wt. % of an aliphatic monoester (e.g., at least 25 wt. % of an aliphatic monoester). In some embodiments, the effluent has a selectivity to an aliphatic monoester of at least 20% (e.g., at least 25%, 30%, 35%, 40% or 45%).

In some embodiments, the effluent comprises a hydrocarbon fraction comprising normal paraffins. In some embodiments, the effluent comprises at least 80 wt. % of normal paraffins. In some embodiments, the normal paraffins have from 8 to 24 carbon atoms (e.g., from 12 to 18 carbon atoms).

Note that the normal paraffins can be utilized as a middle distillate fuel. However, subsequent isomerization of the normal paraffins to isoparaffins can provide a broader range of products, thereby making the process more universal and flexible.

Catalytic Isomerization

In some embodiments, such above-described processes can further comprise a step of catalytically isomerizing at least some of the normal paraffins to form an isomerized product comprising isoparaffins. In some embodiments, the step of catalytically isomerizing results in superior fuel properties (e.g., cloud point, pour point etc.) relative to those of the non-isomerized paraffinic product.

In some embodiments, the step of isomerizing is carried out using an isomerization catalyst. Suitable such isomerization catalysts can include, but are not limited to, Pt and/or Pd on a support. Suitable supports include, but are not limited to, zeolites CIT-1, IM-5, SSZ-20, SSZ-23, SSZ-24, SSZ-25, SSZ-26, SSZ-31, SSZ-32, SSZ-32, SSZ-33, SSZ-35, SSZ-36, SSZ-37, SSZ-41, SSZ-42, SSZ-43, SSZ-44, SSZ-46, SSZ-47, SSZ-48, SSZ-51, SSZ-56, SSZ-57, SSZ-58, SSZ-59, SSZ-60, SSZ-61, SSZ-63, SSZ-64, SSZ-65, SSZ-67, SSZ-68, SSZ-69, SSZ-70, SSZ-71, SSZ-74, SSZ-75, SSZ-76, SSZ-78, SSZ-81, SSZ-82, SSZ-83, SSZ-86, SUZ-4, TNU-9, ZSM-5, ZSM-12, ZSM-22, ZSM-23, ZSM-35, ZSM-48, EMT-type zeolites, FAU-type zeolites, FER-type zeolites, MEL-type zeolites, MFI-type zeolites, MTT-type zeolites, MTW-type zeolites, MWW-type zeolites, TON-type zeolites, other molecular sieves materials based upon crystalline aluminophosphates such as SM-3, SM-7, SAPO-11, SAPO-31, SAPO-41, MAPO-11 and MAPO-31. In some embodiments, the step of isomerizing involves a Pt and/or Pd catalyst supported on an acidic support material selected from the group consisting of beta or zeolite Y molecular sieves, silica, alumina, silica-alumina, and combinations thereof. For other suitable isomerization catalysts, see, e.g., U.S. Pat. Nos. 4,859,312; 5,158,665; and 5,300,210.

Isomerization conditions can include a temperature of from 200° F. to 900° F. (93° C. to 482° C.), e.g., from 300° F. to 800° F. (149° C. to 427° C.), or from 400° F. to 800° F. (204° C. to 427° C.); a total reaction pressure of from 15 to 3000 psig (0.1 to 20.7 MPa gauge), e.g., from 50 to 2500 psig (0.3 to 17.2 MPa gauge); a LHSV of from 0.1 to 10 h$^{-1}$, e.g., from 0.25 to 5 h$^{-1}$; and a hydrogen gas treat rate of from 0.1 to 30 MSCF/bbl, e.g., from 0.2 to 20 MSCF/bbl, or from 0.4 to 10 MSCF/bbl.

With regard to the catalytic isomerization step described above, in some embodiments, the methods described herein can be conducted by contacting the normal paraffins with a fixed stationary bed of catalyst, with a fixed fluidized bed, or with a transport bed. In one embodiment, a trickle-bed operation is employed, wherein such feed is allowed to trickle through a stationary fixed bed, typically in the presence of hydrogen. For an illustration of the operation of such catalysts, see, U.S. Pat. Nos. 6,204,426 and 6,723,889.

In some embodiments, the isomerized product comprises at least 10 wt. % isoparaffins (e.g., at least 30 wt. %, 50 wt. %, or 70 wt. % isoparaffins). In some embodiments, the isomerized product has an isoparaffin to normal paraffin mole ratio of at least 5:1 (e.g., at least 10:1, 15:1, or 20:1).

In some embodiments, the isomerized product has a boiling range of from 250° F. to 1100° F. (121° C. to 593° C.), e.g., from 280° F. to 572° F. (138° C. to 300° C.), or from 250° F. to 1000° F. (121° C. to 538° C.).

In some embodiments, the isomerized product is suitable (or better suited) for use as a transportation fuel. In some such embodiments, the isomerized product is mixed or admixed with existing transportation fuels in order to create new fuels or to modify the properties of existing fuels. Isomerization and blending can be used to modulate and maintain pour point and cloud point of the fuel or other product at suitable values. In some embodiments, the normal paraffins are blended with other species prior to undergoing catalytic isomerization. In some embodiments, the normal paraffins are blended with the isomerized product.

EXAMPLES

The following illustrative examples are intended to be non-limiting.

Example 1

Soybean Oil Feed

Soybean oil was purchased from Lucky Supermarket (El Cerrito, Calif.) under the Sunny Select brand. The soybean feed had an API gravity of 21.6 (0.9223 g/mL). The triglycerides of soybean oil are derived mainly from five fatty acids (see, e.g., D. Firestone, *Physical and Chemical Characteris-* tics of Oils, Fats, and Waxes, 2$^{nd}$ Edition, 2006, AOCS Press, 149). Table 1 discloses the representative ranges of these fatty acids in soybean oil.

TABLE 1

| Fatty acid | Carbon atoms:Double bonds | Weight Percent |
| --- | --- | --- |
| Palmitic acid | 16:0 | 9.7 to 13.3 |
| Stearic acid | 18:0 | 3.0 to 5.4 |
| Oleic acid | 18:1 | 17.7 to 28.5 |
| Linoleic acid | 18:2 | 49.8 to 57.1 |
| α-Linoleic acid | 18:3 | 5.5 to 9.5 |

Examples 2-5

The soybean oil feed from Example 1 was tested under hydroprocessing conditions at several temperatures in a single-stage reactor over an alumina-supported Ni—Mo catalyst available from Chevron Lummus Global. The catalyst had a median pore size of about 8 nm and specific surface area of about 180 m$^2$/g. The reactor conditions include a total reaction pressure of 1900 psig (13.1 MPa gauge), a hydrogen gas rate of 8.0 MSCF/bbl, and a LHSV of 1.0 h$^{-1}$.

The composition of the whole product was determined by gas chromatography (GC) and is set forth in wt. % in Table 2. All liquid paraffinic products were normal paraffins as determined by GC with negligible amounts of isoparaffins formed. Methane and propane were essentially the only other hydrocarbon products. Water, carbon monoxide (CO), and carbon dioxide (CO$_2$) were by-products from hydrodeoxygenation, hydrodecarbonylation and/or hydrodecarboxylation.

TABLE 2

Composition of the Whole Product in Weight Percent

| | Ex. 2 | Ex. 3 | Ex. 4 | Ex. 5 |
| --- | --- | --- | --- | --- |
| Reaction Temperature, ° F. | 400 | 450 | 500 | 550 |
| Products, wt. % | | | | |
| Unconverted triglycerides | 42.4 | 0.2 | <0.5 | <0.5 |
| n-C$_{18}$ paraffin | 1.1 | 14.9 | 68.7 | 69.0 |
| n-C$_{17}$ paraffin | 0.1 | 1.5 | 5.3 | 4.8 |
| n-C$_{16}$ paraffin | 0.3 | 1.4 | 8.3 | 8.5 |
| n-C$_{15}$ paraffin | 0 | 0 | 0.6 | 0.5 |
| C$_{18}$ alcohol | 19.6 | 42.5 | — | — |
| C$_{16}$ alcohol | 0.5 | 4.6 | — | — |
| C$_{18}$ acid | 0.4 | 0.4 | — | — |
| C$_{16}$ acid | 0 | 0 | — | — |
| C$_{18}$-C$_{18}$ ester | 20.9 | 16.7 | — | — |
| C$_{18}$-C$_{16}$ ester | 5.5 | 4.0 | — | — |
| C$_{16}$-C$_{16}$ ester | 0.4 | 0.2 | — | — |
| Unknown heavies | 2.7 | 1.5 | — | — |
| Propane | 2.8 | 4.9 | 4.9 | 4.9 |
| Methane | 0 | 0 | 0.1 | 0.3 |
| H$_2$O | 3.3 | 7.0 | 11.4 | 11.8 |
| CO | 0 | 0 | 0 | 0 |
| CO$_2$ | 0.1 | 0.3 | 0.6 | 0.3 |

The conversion rate of triglycerides and product selectivity of the hydroprocessing runs are set forth in Table 3.

TABLE 3

Conversion of Triglycerides and Product Selectivity

| | Ex. 2 | Ex. 3 | Ex. 4 | Ex. 5 |
| --- | --- | --- | --- | --- |
| Reaction Temperature, ° F. | 400 | 450 | 500 | 550 |
| Conversion of | 57.6 | 99.8 | >99.5 | >99.5 |

TABLE 3-continued

Conversion of Triglycerides and Product Selectivity

| | Ex. 2 | Ex. 3 | Ex. 4 | Ex. 5 |
| --- | --- | --- | --- | --- |
| Triglycerides, wt. % | | | | |
| Product Selectivity, % | | | | |
| n-C$_{18}$ paraffin | 1.9 | 15.0 | 68.7 | 69.0 |
| n-C$_{17}$ paraffin | 0.1 | 1.5 | 5.3 | 4.8 |
| n-C$_{16}$ paraffin | 0.5 | 1.4 | 8.3 | 8.5 |
| n-C$_{15}$ paraffin | 0 | 0 | 0.6 | 0.5 |
| C$_{18}$ alcohol | 34.0 | 42.6 | — | — |
| C$_{16}$ alcohol | 0.8 | 4.6 | — | — |
| C$_{18}$ acid | 0.7 | 0.4 | — | — |
| C$_{16}$ acid | 0 | 0 | — | — |
| C$_{18}$-C$_{18}$ ester | 36.2 | 16.7 | — | — |
| C$_{18}$-C$_{16}$ ester | 9.5 | 4.0 | — | — |
| C$_{16}$-C$_{16}$ ester | 0.6 | 0.2 | — | — |
| Unknown heavies | 4.7 | 1.5 | — | — |
| Propane | 4.9 | 4.9 | 4.9 | 4.9 |
| Methane | 0.1 | 0.1 | 0.1 | 0.3 |
| H$_2$O | 5.8 | 7.0 | 11.4 | 11.8 |
| CO | 0 | 0 | 0 | 0 |
| CO$_2$ | 0.3 | 0.3 | 0.6 | 0.3 |

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A hydrocarbon conversion process, comprising:
    a) contacting a renewable feedstock, under hydroprocessing conditions, with a supported catalyst comprising at least one metal selected from the group consisting of Group VIII metals and Group VIB metals to form an effluent; and b) recovering an aliphatic monoester fraction from the effluent, wherein the hydroprocessing conditions include a temperature of from 383° F. to 464° F. (195° C. to 240° C.) and a total reaction pressure of from 800 to 2000 psig (5.5 to 13.8 MPa gauge).

2. The process of claim 1, having a triglyceride conversion rate of at least 50 wt. %.

3. The process of claim 1, wherein the feedstock comprises at least 50 wt. % triglycerides.

4. The process of claim 1, wherein the feedstock originates from a biomass source selected from the group consisting of crops, vegetables, microalgae, animal fats, and combinations thereof.

5. The process of claim 1, wherein the feedstock is selected from the group consisting of canola oil, coconut oil, palm oil, palm kernel oil, peanut oil, rapeseed oil, soybean oil, and combinations thereof.

6. The process of claim 1, wherein the Group VIII metal is selected from a noble metal, Fe, Co and Ni and the Group VIB metal is selected from the group consisting of Cr, Mo and W.

7. The process of claim 1, wherein the catalyst is selected from the group consisting of a Ni—Mo catalyst, a Ni—W catalyst, a Ni—Mo—W catalyst, a Co—Mo catalyst, and combinations thereof.

8. The process of claim 1, wherein the catalyst is an alumina-supported Ni—Mo catalyst.

9. The process of claim 1, wherein the catalyst has an average pore size of from 1 to 10 nm and a surface area of from 20 to 400 $m^2/g$.

10. The process of claim 1, wherein the pressure is from 1600 to 2000 psig (11.0 to 13.8 MPa gauge).

11. The process of claim 1, wherein the effluent comprises at least 20 wt. % of an aliphatic monoester.

12. The process of claim 1, wherein the effluent comprises at least 25 wt. % of an aliphatic monoester.

13. The process of claim 1, having an aliphatic monoester selectivity in the effluent of at least 20%.

14. The process of claim 1, having an aliphatic monoester selectivity in the effluent of at least 40%.

15. The process of claim 1, wherein the aliphatic monoester has from 18 and 36 carbon atoms.

* * * * *